United States Patent [19]
Poveromo

[11] 4,196,516
[45] Apr. 8, 1980

[54] ATTACHMENTS FOR DENTURES

[76] Inventor: Melvin D. Poveromo, 1160 96 St., Miami Beach, Fla. 33154

[21] Appl. No.: 933,029

[22] Filed: Aug. 11, 1978

[51] Int. Cl.² .............................................. A61C 13/22
[52] U.S. Cl. .................................................... 433/182
[58] Field of Search ...................................... 32/5, 6, 7

[56] References Cited

U.S. PATENT DOCUMENTS

| 2,271,796 | 2/1942 | Eckman | 32/5 |
| 2,803,060 | 8/1957 | Weiss | 32/5 |
| 3,710,446 | 1/1973 | Poveromo | 32/5 |

*Primary Examiner*—Robert Peshock

*Attorney, Agent, or Firm*—Sughrue, Rothwell, Mion, Zinn and Macpeak

[57] ABSTRACT

Denture attachments for establishing a connection between a tooth and an adjoining denture include a female housing anchored in a tooth, a male connector assembly with a housing and an expandable insert. The housing is secured to the denture, and is of reduced height relative thereto, whereby a portion of the denture overlies the housing. The housing is secured to the denture, and the insert is engaged in the female housing.

In a modification, the housing of the male connector assembly has means to effect a secure connection with a mastic type of adhesive bond.

8 Claims, 10 Drawing Figures

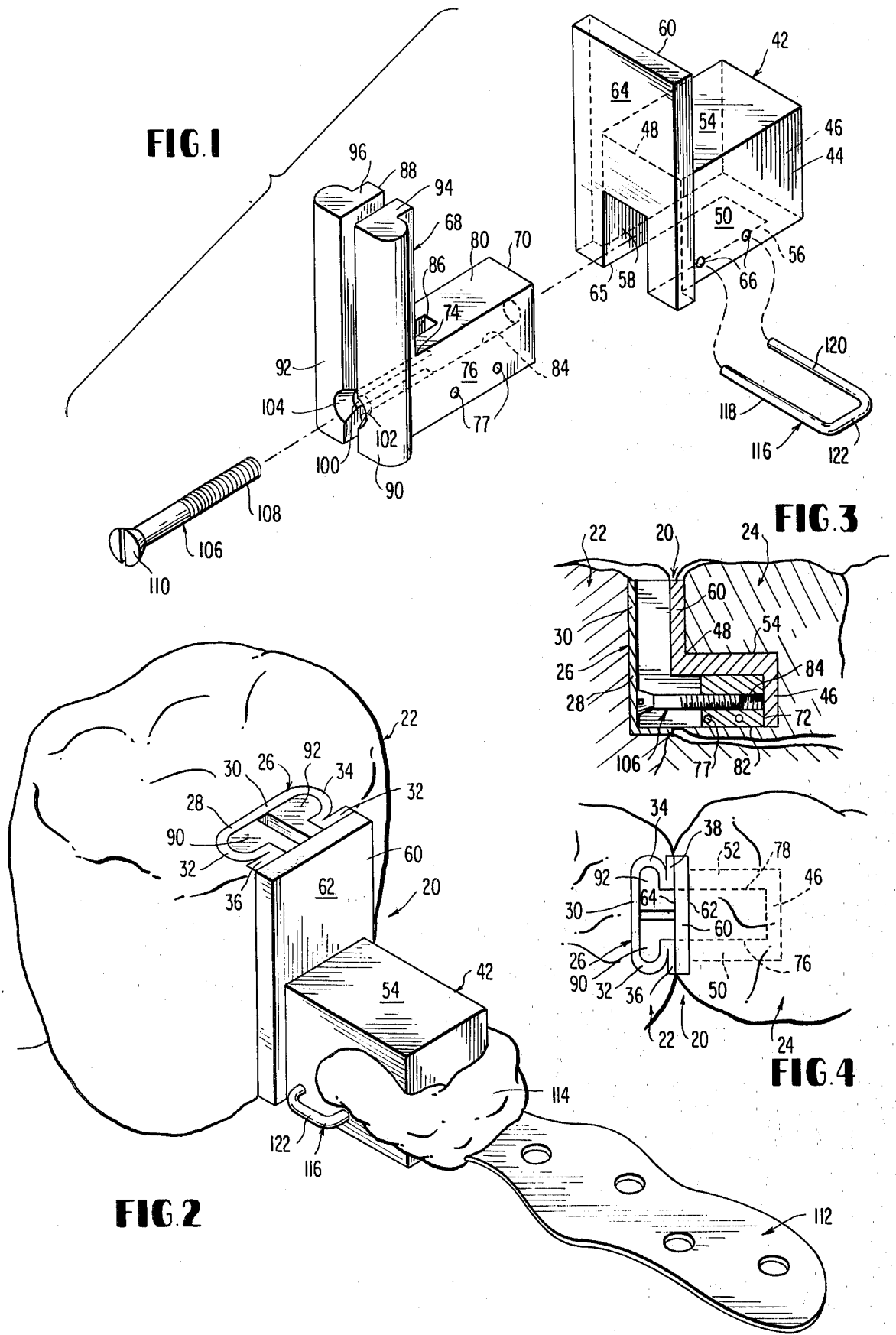

ATTACHMENTS FOR DENTURES

BACKGROUND OF THE INVENTION

1. Field of the Invention

This invention relates to improvements in attachment means for a dental bridge work.

2. Statement of the Prior Art

Denture attachment means which reflect the prior art herein improved are shown in my prior U.S. Pat. Nos. 3,117,377 and 3,710,446.

SUMMARY OF THE INVENTION

In the earlier patents mentioned herein above, an expandable male insert is seated in a female housing. A secure fit is insured by this arrangement, as well as adjustability of positioning of the denture relative to the tooth to which it is attached.

A principal objective of the present invention relates to the provision of an attachment wherein the first tooth of the bridge overlies the shank portion of the attachment assembly. This permits optimum abutment of the bridge to the adjoining tooth, improves the appearance of the connection, and diminishes its bulk. In distinction to prior devices of this nature, the expansion means hererof is located adjacent the base of the insert, with the result that the overall height of the assembly is substantially decreased.

The appearance of the denture is enhanced by the use of this invention in that the connection assembly is hidden by the teeth and is not visible when the unit is installed.

In a modified form of the invention, attachment by acrylic or other plastic adhesives is made feasible by the provision of a special surface on the housing portion of the male connector.

Other and further objects and advantages of the invention will become apparent to those skilled in the art from a consideration of the following specification when read in conjunction with the annexed drawings.

BRIEF DESCRIPTION OF THE DRAWINGS

FIG. 1 is a disassembled perspective view showing the male connection components of a first form of the attachment hereof;

FIG. 2 shows the entire unit with the denture removed;

FIG. 3 is a medial vertical cross section through a finished assembly;

FIG. 4 is a top plan view thereof;

DESCRIPTION OF THE PREFERRED EMBODIMENTS

Figure 5:
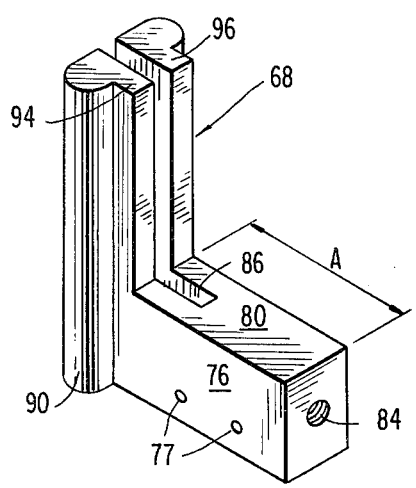
FIG. 5 is a perspective view of the insert portion of the male connector.
Figure 6:
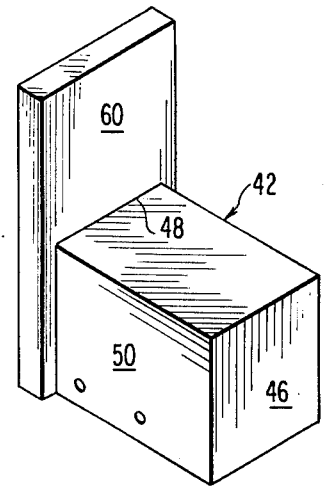
FIG. 6 is a perspective view of the housing portion of the male connector.
Figure 7:
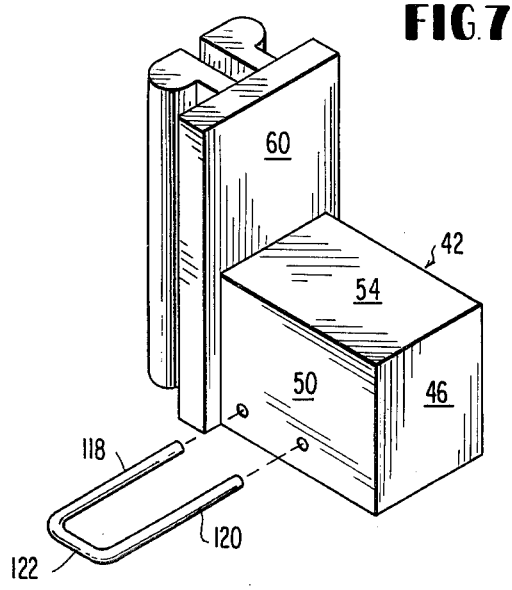
FIG. 7 shows an insert and housing partially assembled.

Referring to the drawings in more detail, FIGS. 2 through 4 illustrate an assembled attachment 20 of this invention. The attachment 20 establishes a connection between a tooth 22 and a denture 24, and comprises male and female interfitting components.

The female connector is identified in the drawings by reference character 26 and comprises a female housing 28 embedded fixedly in a socket formed therefore in the tooth 22. The housing includes a bight portion 30 with rounded arms 32, 34 projecting from its ends in confronting, oppositly curved relation. The arms terminate in reverted outer wings 36, 38 which have flat outer faces substantially parallel to the bight portion 30. The housing thus defines a generally T form chamber.

The male connector assembly 40, shown disassembled in FIG. 1, includes a housing 42 with a substantially rectangular body portion 44 having a rear wall 46, a forward end 48, side walls 50, 52, a top wall 54 and an open base 56. The form of the housing is such that it defines a chamber 58 which is open on the base 56 and the forward end 48. The housing further comprises a substantially vertical male contact face plate 60, preferably of integral formation with the housing. The plate 60 has an inner side 62, and an outer side 64. The plate is of somewhat greater height from top to bottom then housing 42, but includes a bottom rectangular slot 65 aligned with the housing chamber 58.

At least one of the side walls 50, 52 of the housing has a pair of apertures 66 form therein, for a purpose appearing below.

A second component of the connector assembly is a connector head 68. The head 68 has a substantially rectangular shank 70 with a distal end wall 72, a proximal wall 74, sides 76, 78, a top 80, and a base 80. The sides have holes 77 formed therein. The shank has an internally threaded bore 84 extending longintually there through from end to end, and a vertical slot 86 opening on the proximal end. Integrally connected to the proximal end 74 on each side of said slot 86 is a vertical insert member 88 composed of a pair of inserts 90, 92 each being of a configuration to fit within the rounded arms 30, 32 of the female housing and being co-extensive in height therewith. Each of the inserts has a leg 94, 96 extending to the shank 70.

The inserts have opposed, confronting chamber 98, 100, formed therein in alignment with the bore 84, the channels being countersunk or flared at 102, 104.

An elongated screw 106 has a threaded section 108 and an enlarged head 110. The screw serves as a means to laterally expand the inserts during assembly of the unit.

In FIG. 2, a typical installation is shown. There a crib 112 for a denture housing is affixed by solder 114 or the like to the housing 42 of the male connector. The shank 70 of the connector head is inserted through the slot 64 and into the chamber 58 of the housing, and disposed so that the holes 77 are aligned with the apertures 66. A U form brad 116 has legs 118, 120 which are fitted within the aligned apertures and holes as shown, with a bridging element 122 in outwardly spaced to the housing, the outward spacing of the bridging element permits the solder 114 to be engaged thereabout to strengthen the bond. With the female element in place in the tooth, adjustment of the insert to correct size is made by extension of the screw 106 into the bore 84 to a depth such that the head 110 of this screw engages the flared portion 102, 104 of the chambers. This expands the inserts, and when a precise fit is reached, the inserts are seated in the housing with the outer side 64 of the plate 60 flush against the wings 36, 38.

The rear wall 46 of the housing has an inductation there to permit such extension of the screw, as shown in FIG. 3.

Figure 8:
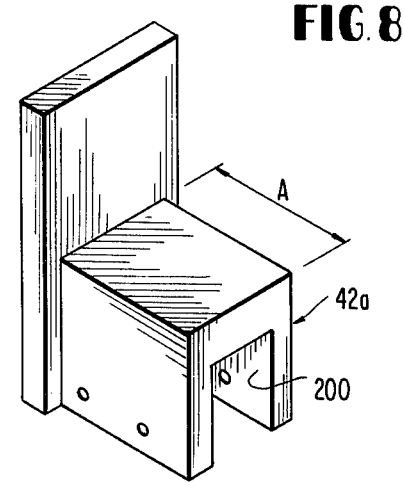
FIG. 8 illustrates the modified version of the housing.

In FIG. 8 a first modified form of the housing, designated 42a, of the male connector is shown. The housing 42a is the same as the housing 42 except that the rear wall 46 is open at 200. This permits adhesion of the acrylic plastic of the denture base or the solder with the screw, thereby further strengthening the connection therebetween.

Figure 10:
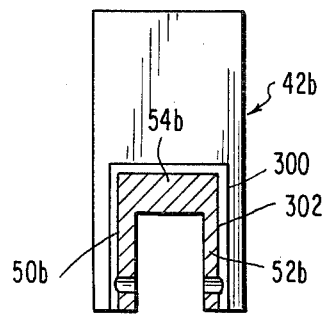
FIG. 10 is a transverse sectional view taken on line 10—10 of FIG. 9, looking in the direction of the arrows.
Figure 9:
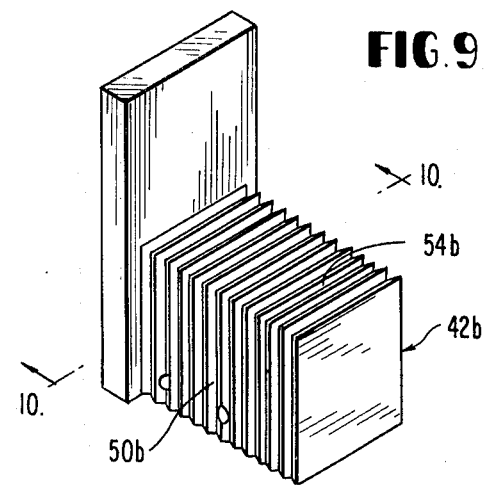
FIG. 9 is a second modified housing.

In FIGS 9 and 10 still another modification of the form of the housing, identified by reference numeral 42b is shown. Here, the side walls 50b, 52b, and the top wall 54b are provided with a continuous series of ridges 300 and slots 302. This arrangement enhances the stability of the attachment when solder, acrylic plastic, or other mastics are employed in that these materials interengage in the grooves. Otherwise, the operation of the modified forms of the invention is as described above with respect to the first illustrated embodiment.

I claim:

1. A denture attachment for establishing a connection between a denture and an adjoining tooth comprising, in combination:
    a female housing having a bight portion, rounded arms arranged in confronting opposite curved positions on the bight portion, and having reverted outer wings with flat faces, the female housing being adapted to be embedded in vertical position in the tooth with the flat faces exposed;
    a male connector assembly including a housing, a connector head, means for securing the connector head to the housing, and means for expanding the head;
    the housing including a substantially rectangular body portion having a rear vertical wall, a forward end, side walls, a top wall and a base, and having a chamber formed therein opening on said base and on the forward end;
    the housing further including a vertical male contact face plate having an inner side, an outer side, and being of increased height relative to the rectangular body, the plate having a slot therein aligned with said chamber and the inner side of the face plate being fixedly secured to the forward end of the body;
    at least one of the side walls of the body having a pair of apertures therein;
    the connector including a shank of substantially rectangular form having a distal end wall, sides, a proximal end, a top and a base, and a threaded bore extending longitudinally thereto from the proximal end to the distal end wall;
    the shank having a vertically extending slot opening on said proximal end;
    an elongated vertical insert member integrally connected to the shank proximal end on each side of the slot, said insert member being of a configuration to slideably engage in the curved portions of the female housing and being co-extensive in height therewith;
    the vertical member including inserts having opposed, confronting channels formed therein, flared outwardly at their ends;
    the means for expanding the head comprising a screw threadedly engaged in the threaded bore of the shank and extending through the channels, the screw having an enlarged head to fit within the flared ends of the channel to expand the inserts outwardly; and
    the shank having transverse holes formed therein aligned with the apertures of the housing; the means for securing the shank to the housing comprising a brad extending through said holes and apertures.

2. The invention of claim 1, wherein:
    the housing top and side walls are serrated and have alternating grooves and ridges.

3. The invention of claim 1, wherein:
    the rear wall of the housing body portion has a recess therein to admit said screw.

4. The invention of claim 1, wherein:
    the rear wall of the housing body portion has a rectangular slot therein to expose the screw.

5. The invention of claim 1, and:
    an adhesive substance bonding the denture to the housing with the denture partially overlying the housing.

6. The invention of claim 4, and:
    an adhesive substance bonding the denture to the housing with the denture partially overlying the housing and engaging the screw within the housing.

7. In a denture attachment having a female housing embedded in a tooth, and a male connector assembly including a housing secured to a denture and a connector head, the improvement wherein:
    said housing comprises a body portion having a chamber therein and having a forward end and a rear wall; a vertical face plate on the forward end of the housing; the vertical face plate being of increased height relative to the housing; a connector head including a shank and insert members forming a second component of the male connector assembly; the shank being seated in the housing and the insert members being coextensive in height with said vertical face plate and engaged in the female housing.

8. The improvement of claim 7, wherein:
    the female housing includes exposed reverted outer wings with flat faces; and
    the vertical face plate being disposed in abutting relation to said face plate.

* * * * *